United States Patent
Hense et al.

(10) Patent No.: US 7,365,098 B2
(45) Date of Patent: Apr. 29, 2008

(54) N'-CYANO-N-METHYL-IMIDAMIDE DERIVATIVES

(75) Inventors: Achim Hense, Sulzbach (DE); Rüdiger Fischer, Pulheim (DE); Ernst R. F. Gesing, Erkrath (DE); Stefan Herrmann, Langenfeld (DE); Kristian Kather, Langenfeld (DE); Christoph Erdelen, deceased, late of Leichlingen (DE); by Angelika Lubos-Erdelen, legal representative, Leichlingen (DE); Jörg Konze, Köln (DE); Peter Lösel, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 570 days.

(21) Appl. No.: 10/514,365

(22) PCT Filed: May 8, 2003

(86) PCT No.: PCT/EP03/04808

§ 371 (c)(1),
(2), (4) Date: May 2, 2005

(87) PCT Pub. No.: WO03/095418

PCT Pub. Date: Nov. 20, 2003

(65) Prior Publication Data

US 2006/0035978 A1 Feb. 16, 2006

(30) Foreign Application Priority Data

May 13, 2002 (DE) .................. 102 21 121

(51) Int. Cl.
C07C 261/04 (2006.01)
A01N 47/40 (2006.01)
(52) U.S. Cl. ...................... 514/609; 558/391
(58) Field of Classification Search ............. 558/391; 514/609
See application file for complete search history.

(56) References Cited

U.S. PATENT DOCUMENTS

| | | | |
|---|---|---|---|
| 4,921,955 A | 5/1990 | Töpfl | 544/60 |
| 5,185,351 A | 2/1993 | Finkelstein et al. | 514/341 |
| 5,304,566 A | 4/1994 | Ishimitsu et al. | 514/357 |
| 5,418,250 A | 5/1995 | Finkelstein et al. | 514/397 |
| 5,612,358 A | 3/1997 | Ishimitsu et al. | 514/357 |
| 6,063,813 A | 5/2000 | Bayer et al. | 514/506 |
| 6,638,979 B1 * | 10/2003 | Riebel et al. | 514/609 |

FOREIGN PATENT DOCUMENTS

| | | |
|---|---|---|
| WO | 93/04032 | 4/1993 |
| WO | 94/29268 | 12/1994 |
| WO | 00/03976 | 1/2000 |

OTHER PUBLICATIONS

J. Organomet. Chem., 97 (month unavailable) 1975, pp. 39-44, Eugene J. Kupchik et al, "Reactions of Thioamides with Bis(Triphenylstannyl)-Carbodiimide and (Triphenylstan-ny)Cyanamide".

Bull. Soc. Chim. Belg., 90(1), (month unavailable) 1981, pp. 89-98, Gerrit L'abbé et al, "Synthesis of Symmetrical 1,6-Dihetero-6aλ$_4$-Thia-3,4-Diazapentalenes from 5-Amino-1,2,3,4-Thiatriazole".

J. Chem. Soc. Perkin Trans. I, (month unavailable) 1983, pp. 1049-1061, Ken Chantrapromma et al, "Base Catalysed Rearrangements involving Ylide Intermediates. Part 18. Competing [1,2], [1,3], and [1,4] Rearrangements of Ammonium Ylides".

J. Org. Chem., 65, (month unavailable) 2000, pp. 3971-3981, Charles P. Salerno et al, "Enzymatic Synthesis of Caged NADP Cofactors: Aqueus NADP Photorelease and Optical Properties".

J. Med. Chem., 26, (month unavailable) 1983, pp. 1353-1360, David C. Atkinson et al, "Substituted (2-Phenoxyphenyl)acetic Acids with Antiinflammatory Activity".

Bull. Chem. of Jpn., 60, (month unavailable) 1987, pp. 767-768, Masanori Kosugi et al, (α-Ethoxyvinyl)tributyltin; An Efficient Reagent for the Nucleophlic Acetylation of Organic Halides via Palladium Catalysis.

J. Org. Chem., 28, (month unavailable) 1963, pp. 1816-1821, K. Robert Huffman et al, N-Cyanoimidates.

J. Prakt. Chem., 318, (month unavailable) 1976, pp. 347-349, H. Schäfer et al, "Einstufige Synthese von Arylaminomethylen-cyanamiden".

Helv. Chim. Acta., vol. 58, (month unavailable) 1975, pp. 2192-2209, Albrecht Edenhofer, "Über einen neuen Zugang zu imidazolen, sowie deren Verwendung zur Synthese von Purinen und 4,6-Dihydro-1,2-dimethyl-8-phenylimidazo[4,5-e]-1,4-diazepin-5(1H)-on".

* cited by examiner

Primary Examiner—Fiona T Powers
(74) Attorney, Agent, or Firm—Richard E. L. Henderson

(57) ABSTRACT

The present invention relates to novel N'-cyano-N-methylimidamide derivatives of the general formula (I)

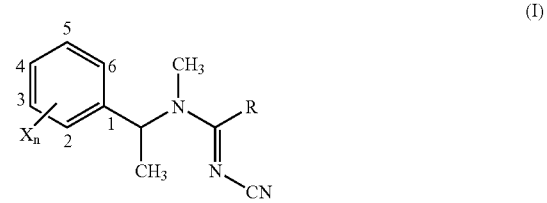

in which
n represents 2, 3, 4 or 5,
R represents optionally halogen-substituted $C_1$-$C_4$-alkyl, and
X represents halogen, where the substituents X may in each case be identical or different,
to processes for their preparation and to their use as pesticides.

10 Claims, No Drawings

N'-CYANO-N-METHYL-IMIDAMIDE DERIVATIVES

The present patent application has been filed under 35 U.S.C. 371 as a national stage application of PCT/EP03/04808, filed May 8, 2003, which was published in German as International Patent Publication WO 03/095418 on Nov. 20, 2003, which is entitled to the right of priority of German Patent Application 102 21 121.3, filed May 13, 2002.

The present invention relates to novel N'-cyano-N-methylimidamide derivatives, to a process for their preparation and to their use for controlling animal pests.

Certain N'-cyano-N-methylimidamide derivatives are already known (cf. WO 91/04 965, WO 93/04032, EP 0 403 159 A2; DE 195 48 783 A1, *J. Organomet. Chem.* (1975), 97 (1), pp. 39-44; *Bull. Soc. Chim. Belg.* (1981), 90 (1), pp. 89-98 and in particular WO 00/03976). Insecticide properties of some of these compounds are also known (cf. EP 0 314 852 A1).

However, the activity of these compounds is not in every respect entirely satisfactory. Accordingly, it was an object of the present invention to provide further compounds having convincing activity against pests.

This invention now provides novel imidamide derivatives of the general formula (I)

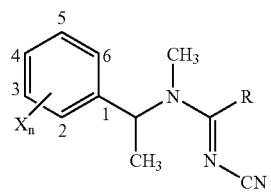
(I)

in which
n represents 2, 3, 4 or 5,
R represents optionally halogen-substituted $C_1$-$C_4$-alkyl, and
X represents halogen, where the different substituents X may in each case be identical or different.

The N'-cyano-N-methylimidamide derivatives of the formula (I) can be present as optical and/or geometrical isomers. The present invention relates both to the different isomer mixtures and, in particular, to the pure isomers of the compounds according to the invention.

The novel N'-cyano-N-methylimidamide derivatives of the general formula (I) are obtained when amines of the formula (II)

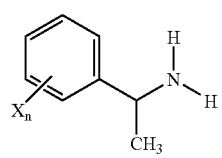
(II)

in which
X and n are as defined above, are reacted
(a) with N-cyanoalkylimidic acid esters of the formula (III)

(III)

in which
R is as defined above,
Q represents oxygen or sulfur and
Y represents alkyl, in the presence of a diluent, or
(a') with orthoesters of the formula (IV)

(IV)

in which
R is as defined above, and
Y represents alkyl, and cyanamide, if appropriate in the presence of a diluent, and
(b) subsequently alkylated by reacting the compounds, obtained according to process (a) or (a'), of the formula (V)

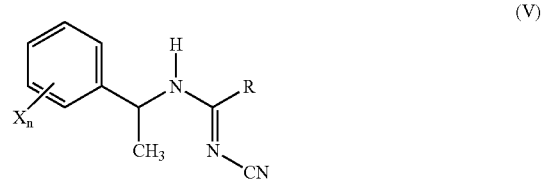
(V)

in which
R, X and n are as defined above,
with compounds of the formula (VI)

$$CH_3\text{-}Z \quad (VI)$$

in which
Z represents a leaving group, for example halogen (for example chlorine, bromine or iodine), mesylate or tosylate.

However, it is also possible to obtain the compounds of the formula (I) by reacting N-methylated amines of the formula (VII)

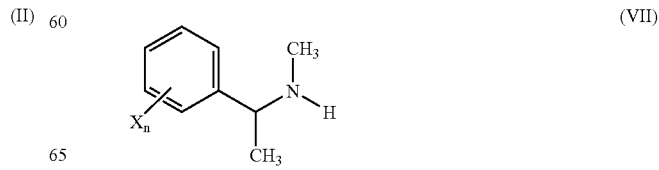
(VII)

in which

X and n are as defined above, with N-cyanoalkylimidic acid esters of the formula (III) according to process (a) or with orthoesters of the formula (IV) and Cyanamide according to process (a'), the subsequent alkylation being applicable.

The novel N'-cyano-N-methylimidamide derivatives of the general formula (I) have strongly pronounced biological properties and are suitable especially for controlling animal pests, such as insects, arachnids, in particular nematodes, encountered in agriculture, in forests, in the protection of stored products and materials and also in the hygiene sector.

The formula (I) provides a general definition of the compounds according to the invention. Preferred substituents and ranges of the radicals listed in the formulae given above and below are illustrated below.

n preferably represents 2, 3 or 4.

R preferably represents optionally fluorine-, chlorine- or bromine-substituted methyl, ethyl, n- or i-propyl or n-, i-, s- or t-butyl.

X preferably represents fluorine, chlorine or bromine.

If n represents 2, a first substituent X is preferably in the ortho-position (2) and a second substituent X is preferably in the para-position (4), or a first substituent X is preferably in the meta-position (3) and a second substituent X is preferably in the para-position (4).

If n represents 3, a first substituent X is preferably in the ortho-position (2), a second substituent X is in the para-position (4) and a third substituent X is in the meta-position (5) on the phenyl ring.

n particularly preferably represents 2 or 3.

R particularly preferably represents optionally fluorine- or chlorine-substituted methyl, ethyl or n- or i-propyl.

X particularly preferably represents fluorine or chlorine.

If n represents 2, a first substituent X is particularly preferably in the ortho-position (2) and a second substituent X is particularly preferably in the para-position (4).

R very particularly preferably represents methyl or ethyl.

Particularly preferred compounds in the context of the above definitions of substituents are compounds of the formulae (IA) to (IE):

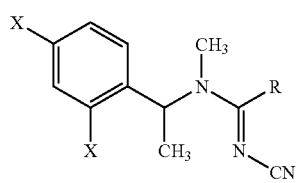
(IA)

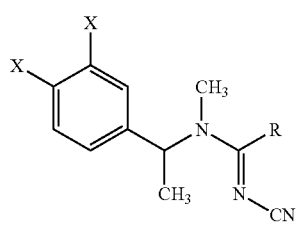
(IB)

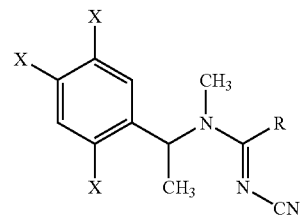
(IC)

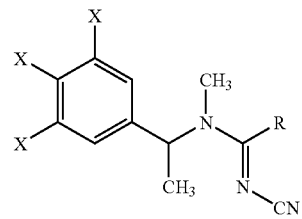
(ID)

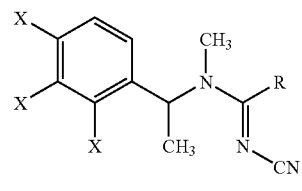
(IE)

Very particularly preferred compounds in the context of the above definitions of substituents are compounds of the following formulae (IA$^1$) to (IE$^7$):

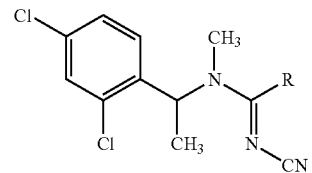
(IA$^1$)

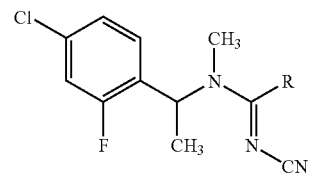
(IA$^2$)

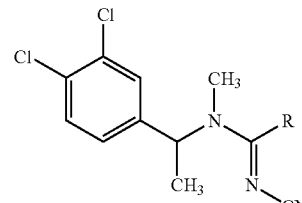
(IB$^1$)

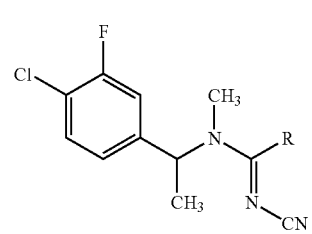
(IB$^2$)

-continued
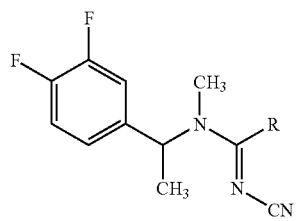 (IB³)
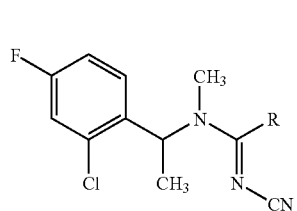 (IB⁴)
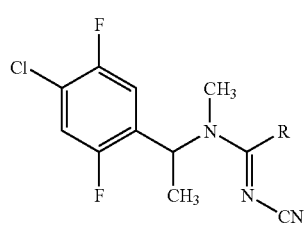 (IA³)
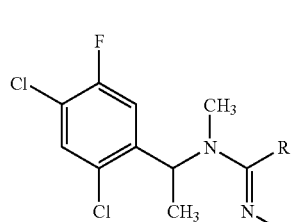 (IA⁴)
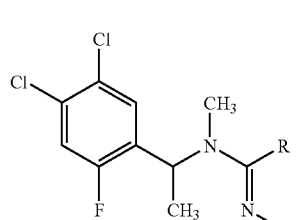 (IC¹)
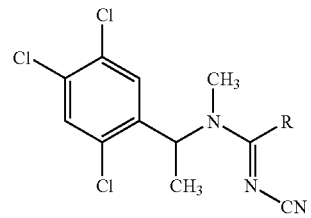 (IC⁴)
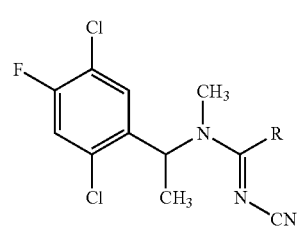 (IC⁵)
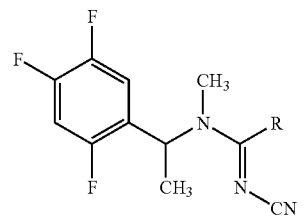 (IC⁶)
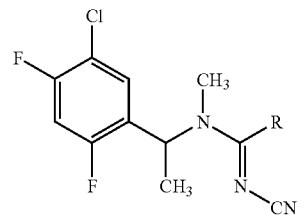 (IC⁷)
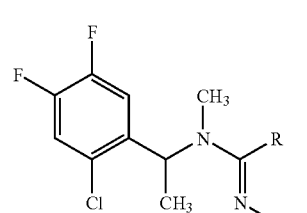 (IC⁸)
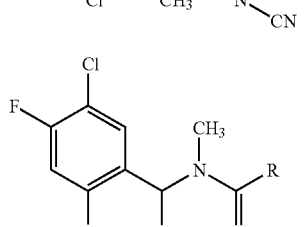 (IC⁹)
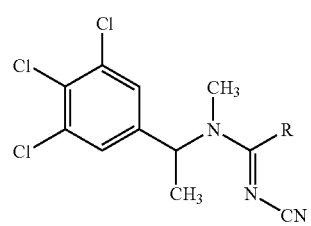 (ID¹)

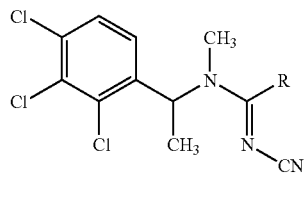
(ID²)
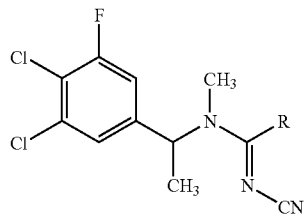
(IE²)
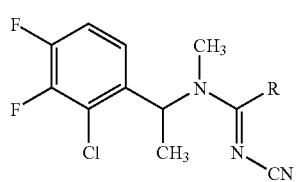
(ID³)
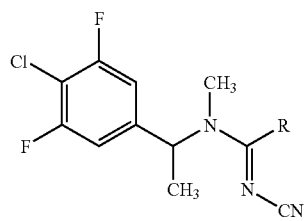
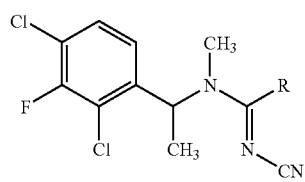
(ID⁴)
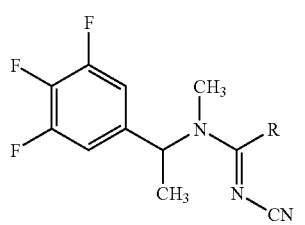
(IE⁴)
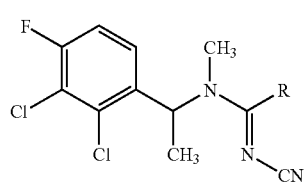

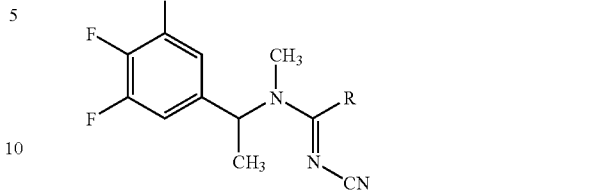
(IE¹)

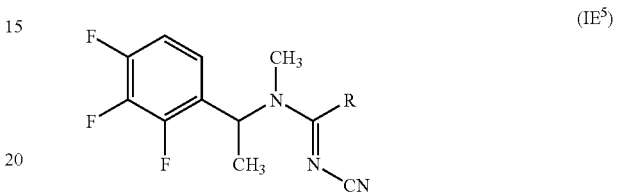
(ID⁵)

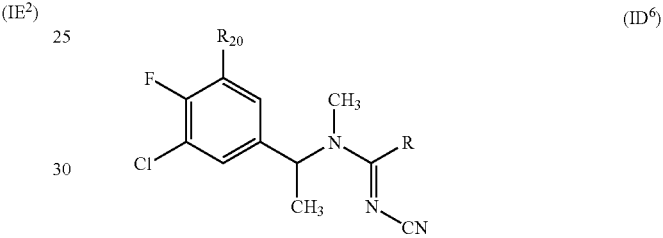
(IE⁵)

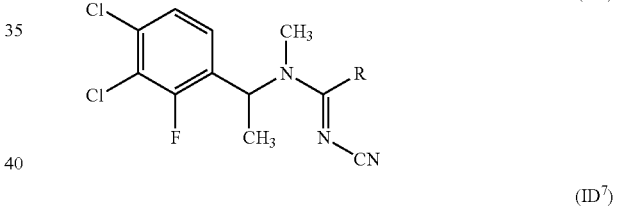
(ID⁶)

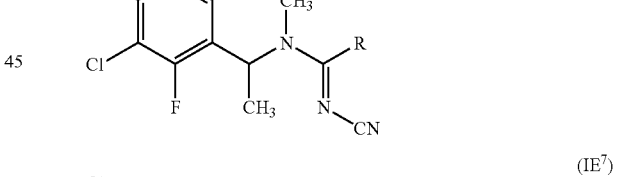
(IE⁶)

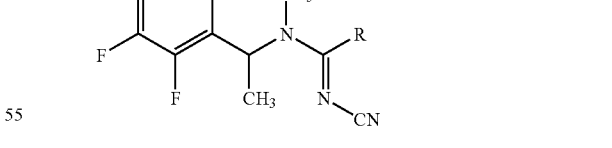
(ID⁷)

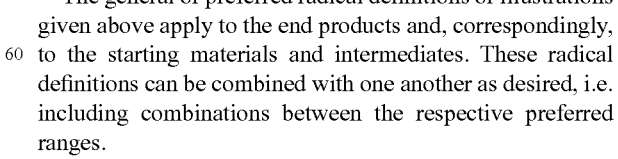
(IE⁷)

The general or preferred radical definitions or illustrations given above apply to the end products and, correspondingly, to the starting materials and intermediates. These radical definitions can be combined with one another as desired, i.e. including combinations between the respective preferred ranges.

Preference according to the invention is given to the compounds of the formula (I) which contain a combination of the meanings listed above as being preferred.

Particular preference according to the invention is given to the compounds of the formula (I) which contain a combination of the meanings given above as being particularly preferred.

Very particular preference according to the invention is given to the compounds of the formula (I) which contains a combination of the meanings given above as being very particularly preferred.

In the radical definitions listed above and below, hydrocarbon radicals, such as alkyl, are in each case straight-chain or branched as far as this is possible.

The amines of the general formula (II) and (VII) to be used as starting material in the process according to the invention are generally known compounds of organic chemistry and/or can be obtained in a generally known manner, for example according to Houben-Weyl, Methoden der organischen Chemie [Methods of organic chemistry], Volume XI, 1; Chantrapromma et al., *J. Chem. Soc. Perkin Trans.* 1 (1983), 1049-1062; Salerno et al., *J. Org. Chem.* 65 (2000), 3971-3981; Atkinson et al., *J. Med. Chem.* 26 (1983), 1353-1360; Kosugi et al., *Bull. Chem. Soc. Jpn.*, 60 (1987), 767-68.

The formula (III) provides a general definition of the N-cyanoalkylimidic acid esters also required as starting materials for carrying out the process (a) according to the invention. In this formula, Y preferably represents $C_1$-$C_4$-alkyl, in particular methyl or ethyl.

Most of the N-cyanoalkylimidic acid esters are known (cf., for example, U.S. Pat. No. 5,304,566 or *J. Org. Chem.* 28, 1963, 1816-1821) and/or they can be obtained by customary processes.

The formula (IV) provides a general definition of the orthoesters also required as starting materials for carrying out the process (a') according to the invention. In this formula, Y preferably represents $C_1$-$C_4$-alkyl, in particular methyl or ethyl.

The compounds of the formula (IV) are compounds known to the person skilled in the art (cf. also Schäfer and Gewald, *J. Prakt. Chem.* 318, 1976, 347-349).

The compounds of the formula (VI) used for the alkylation (methylation) of compounds of the formula (V) are likewise known compounds.

The process (a') according to the invention can be carried out, for example, analogously to Schäfer and Gewald, *J. Prakt. Chem.* 318, 1976, 347-349, which describes the synthesis of arylaminoethylene cyanamides.

As described above, the processes (a) and (a') according to the invention can also be carried out using N-methylated amines of the formula (VII) as starting materials (see, for example, Edenhofer, *Helv. Chim. Acta* 58, 1975, 2192-2209); in this case, the subsequent methylation is not applicable.

The processes according to the invention are preferably carried out in the presence of a diluent which, in the case of process (a'), is not necessarily required. Preference is given to using alcohols, such as methanol and ethanol; nitriles, such as acetonitrile; or esters, such as ethyl acetate. If appropriate, it may also be possible to carry out the processes according to the invention in water or organic-aqueous mixtures.

When carrying out the processes according to the invention, the reaction partners are preferably employed in equimolar amounts; however, it is also possible to use an excess of one or the other starting material.

When carrying out the processes according to the invention, the reaction temperatures can be varied within a relatively wide range. In general, the processes are carried out at temperatures between 0° C. and 180° C., preferably between 20° C. and 150° C., particularly preferably between 20° C. and 80° C.

Work-up and isolation of the end products are carried out in a manner known to the person skilled in the art.

The active compounds are suitable for controlling animal pests, in particular insects, arachnids and nematodes, which are encountered in agriculture, in forestry, in the protection of stored products and of materials, and in the hygiene sector, and have good plant tolerance and favorable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylustella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella,*

*Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus* and *Latrodectus mactans*.

From the order of Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursa phelenchus* spp.

In particular, the compounds of the formula (I) according to the invention have good nematicidal activity. Thus, they can be employed with particularly good results for controlling Meloidogyne incognita.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds according to the invention can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

At appropriate application rates, some of the compounds according to the invention have herbicidal activity.

These formulations are produced in a known manner, for example by mixing the active compounds according to the invention with extenders, that is liquid solvents and/or solid carriers, optionally with the use of surfactants, that is emulsifiers and/or dispersants and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulfoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, corn cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its customary formulations and in the use forms, prepared from these formulations, as a mixture with other active compounds, such as insecticides, attractants, sterilants, bactericides, acaricides, nematicides, fungicides, growth-regulating substances or herbicides. Insecticides include, for example, phosphoric acid esters, carbamates, carboxylic esters, chlorinated hydrocarbons, phenyl ureas, compounds prepared by microorganisms, inter alia.

Particularly advantageous co-components are, for example, the following:

Fungicides:

aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulfide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminum, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulfate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulfur and sulfur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-b-propyl-1H-1,2,4-triazole-1-ethanol, α-(2,4-dichlorophenyl)-β-methoxy-a-methyl-1H-1,2,4-triazole-1-ethanol, α-(5-methyl-1,3-dioxan-5-yl)-β-[[4-(trifluoromethyl)phenyl]methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxyphenylacetamide, 1-isopropyl {2-methyl-1-[[[1-(4-methylphenyl)ethyl]amino]carbonyl]propyl}carbamate, 1-(2,4-dichlorophenyl)-2-(1H-1,2,4-triazol-1-yl)ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)sulfonyl]-4-methyl-benzene, 1-[[2-(2,4-dichlorophenyl)-1,3-dioxolan-2-yl]methyl]-1H-imidazole, 1-[[2-(4-chlorophenyl)-3-phenyloxiranyl]methyl]-1H-1,2,4-triazole, 1-[1-[2-[(2,4-dichlorophenyl)methoxy]phenyl]ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)ethyl]-1-ethyl-3-methylcyclopropanecarboxamide, 2,6-dichloro-5-(methylthio)-4-pyrimidinylthiocyanate, 2,6-dichloro-N-(4-trifluoromethylbenzyl)benzamide, 2,6-dichloro-N-[[4-(trifluoromethyl)phenyl]methyl]benzamide, 2-(2,3,3-triiodo-2-propenyl)-2H-tetrazole, 2-[(1-methylethyl)sulfonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)acetamide, 2-phenylphenol (OPP), 3,4-dichloro-1-[4-(difluoromethoxy)phenyl]-1H-pyrrole-2,5-dione, 3,5-dichloro-N-[cyano[(1-methyl-2-propynyl)oxy]methyl]benzamide, 3-(1,1-dimethylpropyl-1-oxo-1H-indene-2-carbonitrile, 3-[2-(4-chlorophenyl)-5-ethoxy-3-isoxazolidinyl]pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulfate, 9H-xanthene-2-[(phenylamino)carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)cycloheptanol, cis-4-[3-[4-(1,1-dimethylpropyl)phenyl-2-methylpropyl]-2,6-dimethylmorpholine hydrochloride, ethyl [(4-chlorophenyl)azo]cyanoacetate, potassium bicarbonate, methanetetrathiolsodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methylcyclohexanecarboxamide, N-(2,6-dimethylphenyl)-2-methoxy-N-(tetrahydro-2-oxo-3-furanyl)acetamide, N-(2,6-dimethylphenyl)-2-methoxy-N-(tetrahydro-2-oxo-3-thienyl)acetamide, N-(2-chloro-4-nitrophenyl)-4-methyl-3-nitro-benzenesulfonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)acetamide, N-(6-methoxy-3-pyridinyl)-cyclopropanecarboxamide, N-[2,2,2-trichloro- 1-[(chloroacetyl)amino]ethyl]-benzamide, N-[3-chloro-4,5-bis(2-propinyloxy)phenyl]-N'-methoxy-methanimidamide, N-formyl-N-hydroxy-DL-alaninesodium salt, O,O-diethyl [2-(dipropylamino)-2-oxoethyl]ethylphosphoramidothioate, O-methyl S-phenyl phenylpropylphosphoramidothioate, S-methyl 1,2,3-benzothiadiazole-7-carbothioate, spiro[2H]-1-benzopyran-2,1'(3'H)-isobenzofuran-3'-one.

Bactericides:
Bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/acaricides/nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184699, cloethocarb, clorethoxyfos, chlordenvinphos, chlorfluazuron, chlormephos, chlorpyrifos, chlorpyrifos M, cis-resmethrin, clocythrin, clofentezin, cyanophos, cycloprothrin, cyflurthrin, cyhalotrin, cyhexatin, cypermethrin, cyromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, ediphenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos, RH 5992, salithion, sebufos, silafluofen, sulfotep, sulprofos, spinosad, tebufenozide, tebufenpyrad, tebupirimphos, teflubenzuron, tefluthrin, temephos, terbam, terbufos, tetrachlorovinphos, thiafenox, thiodicarb, thiofanox, thiomethon, thionazin, thuringiensin, tralomethrin, triarathen, triazophos, triazuron, trichlorfon, triflumuron, trimethacarb, thiamethoxam, vamidothion, XMC, xylylcarb, YI 5301/5302, zetamethrin.

It is also possible to admix other known active compounds, such as herbicides, fertilizers and growth regulators.

When used as insecticides and nematicides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

At appropriate application rates, the compounds according to the invention also have herbicidal properties and/or a plant-growth-regulating action, such as, for example, a defoliant effect.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chori-*

*optes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of from 1 to 80% by weight, directly or after 100 to 10 000-fold dilution, or they can be used as a chemical bath.

It has furthermore been found that the compounds of the formula (I) according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood paneling, wooden window frames and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture or an aliphatic polar organic chemical solvent or solvent mixture is replaced. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odor correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulfonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in Wo 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinylbutyl carbamate, N-octylisothiazolin-3-one and 4,5-dichloro-N-octyl-isothiazolin-3-one.

As already metioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. By plant cultivars are meant plants having new properties ("traits"), bred either by conventional breeding, by mutagenesis or by recombinant DNA techniques. They may be cultivars, biotypes and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The preferred transgenic plants or plant cultivars (i.e. those obtained by genetic engineering) which are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), corn, soybeans, potatoes, cotton, oilseed rape and also fruit plants (with the fruits apples, pears, citrus fruits and grapevines), and particular emphasis is given to corn, soybeans, potatoes, cotton and oilseed rape. Traits that are emphasized are in particular increased defense of the plants against insects by toxins formed in the plants, in particular those formed by the genetic material from Bacillus thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are increased defense of plants against fungi, bacteria and viruses by systematic acquired resistance (SAR), systemine, phytoalexins, elicitors and resistance genes and corresponding expressed proteins and toxins. Traits that are furthermore particularly emphasized are the increased tolerance of the plants to certain herbicidally active compounds, for example imidazolinones, sulfonylureas, glyphosate or phosphinotricin (for example the "PAT" gene). The genes which impart the desired traits in question can also be present in combination with one another in the transgenic plants. Examples of "Bt plants" which may be mentioned are corn varieties, cotton varieties, soybean varieties and potato varieties which are sold under the trade names YIELD GARD® (for example corn, cotton, soybeans), KnockOut® (for example corn), StarLink® (for example corn), Bollgard® (cotton), Nucotn® (cotton) and NewLeaf® (potato). Examples of herbicide-tolerant plants which may be mentioned are corn varieties, cotton varieties and soybean varieties which are sold under the trade names Roundup Ready® (tolerance to glyphosate, for example corn, cotton, soybean), Liberty Link® (tolerance to phosphinotricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned include the varieties sold under the name Clearfield® (for example corn). Of course, these statements also apply to plant cultivars having these or still to be developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The preparation and the use of the active compounds according to the invention is shown in the examples below.

PREPARATION EXAMPLES

Example 1

(Process (a'))

N'-Cyano-N-[1-(2,4-dichlorophenyl)ethyl]propaneimidamide (intermediate of formula (V))

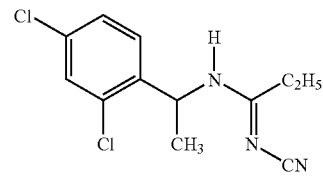

1.85 g of 1-(2,4-dichlorophenyl)ethylamine, 1.63 g of trimethyl orthopropionate and 0.46 g of Cyanamide were heated under reflux for about 30 minutes. The volatile components were removed under reduced pressure and the residue was then titrated with water. Filtration and drying gave 2.22 g of N'-cyano-N-[1-(2,4-dichlorophenyl)ethyl] propaneimidamide of logP of 2.56.

Example 2

(Process (b))

N'-Cyano-N-[1-(2,4-dichlorophenyl)ethyl]-N-methylpropaneimidamide

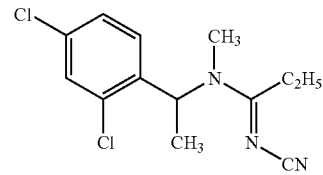

1.00 g of N'-cyano-N-[1-(2,4-dichlorophenyl)ethyl]propaneimidamide was dissolved in 25 ml of dimethylformamide, and 0.16 g of sodium hydride (60% pure in paraffin oil) was added at room temperature. After 30 minutes, 0.63 g of iodomethane was added. The mixture was stirred at room temperature overnight and, after removal of the solvent, purified chromatographically. This gave 0.86 g of N'-cyano-N-[1-(2,4-dichlorophenyl)ethyl]-N-methylpropaneimidamide of logP 2.80 and m.p. 148° C.

Analogously to examples 1 and 2 in accordance with the general description of the preparation processes according to the invention, it is also possible to prepare, for example, the compounds of the general formula (I) listed in table 1 below.

TABLE 1

| Ex. No. | Compound | Physical data |
|---|---|---|
| 3 | (4-Cl, 2-F phenyl, R=CH₃) | m.p.: 101° C. |
| 4 | (4-Cl, 2-F phenyl, R=C₂H₅) | m.p.: 102° C. |
| 5 | (4-Cl, 2,5-F₂ phenyl, R=C₂H₅) | m.p.: 104° C. |
| 6 | (4-Cl, 2,5-F₂ phenyl, R=CH₃) | m.p.: 129° C. |
| 7 | (4-Cl, 3-F phenyl, R=CH₃) | logP: 2.40 |
| 8 | (4-Cl, 3-F phenyl, R=C₂H₅) | logP: 2.61 |
| 9 | (4-Cl, 2,5-F,Cl phenyl, R=C₂H₅) | m.p.: 125° C. |
| 10 | (4-Cl, 2-F phenyl (S), R=C₂H₅) | logP: 2.55 |
| 11 | (4-Cl, 2-F phenyl (R), R=C₂H₅) | logP: 2.55 |
| 12 | (4-Cl, 2,5-F₂ phenyl (S), R=C₂H₅) | logP: 2.59 |
| 13 | (4-Cl, 2,5-F₂ phenyl (R), R=C₂H₅) | logP: 2.59 |

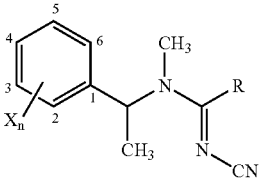

TABLE 1-continued
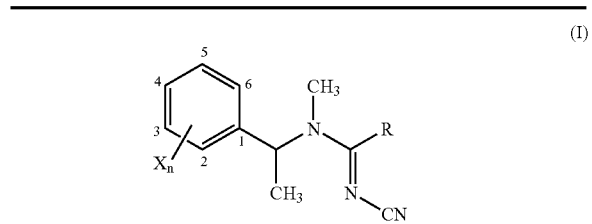
(I)
| Ex. No. | Compound | Physical data |
|---|---|---|
| 14 | | logP: 2.68 |
| 15 | | logP: 2.90 |
| 16 | | logP: 2.31 |
| 17 | | logP: 2.58 |
| 18 | | m.p.: 146-148° C. |
| 19 | | logP: 2.90 |
TABLE 1-continued
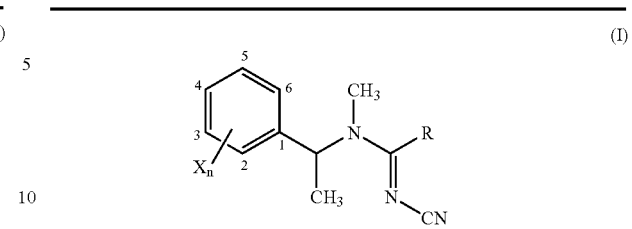
(I)
| Ex. No. | Compound | Physical data |
|---|---|---|
| 20 | | logP: 3.18 |
| 21 | | logP: 2.94 |
| 22 | | logP: 2.19 |
| 23 | | logP: 2.40 |
| 24 | | logP: 2.46 |
| 25 | | logP: 2.94 |

TABLE 1-continued (I) [Structure: phenyl ring with positions 1-6, Xn substituent, attached to CH(CH3)-N(CH3)-C(R)=N-CN]

| Ex. No. | Compound | Physical data |
|---|---|---|
| 26 | [3,4-difluorophenyl-CH(CH3)-N(CH3)-C(CH3)=N-CN] | logP: 2.09 |
| 27 | [3,4-difluorophenyl-CH(CH3)-N(CH3)-C(C2H5)=N-CN] | logP: 2.32 |
| 28 | [2,3-dichlorophenyl-CH(CH3)-N(CH3)-C(CH3)=N-CN] | logP: 2.37 |
| 29 | [2,3-dichlorophenyl-CH(CH3)-N(CH3)-C(C2H5)=N-CN] | logP: 2.59 |
| 30 | [4-Br-2,5-difluorophenyl-CH(CH3)-N(CH3)-C(C2H5)=N-CN] | logP: 2.66 |

The logP values given in table 1 were determined in accordance with EEC-Directive 79/831 Annex V.A8 by HPLC (High Performance Liquid Chromatography) on a reversed-phase column (C 18). Temperature: 43° C.

Mobile phases for the determination in the acidic range: 0.1% aqueous phosphoric acid, acetonitrile; linear gradient from 10% acetonitrile to 90% acetonitrile.

Calibration was carried out using unbranched alkan-2-ones (having 3 to 16 carbon atoms) whose logP values are known (determination of the lopP values by the retention times using linear interpolation between two successive alkanones).

USE EXAMPLES

Example A

Meloidogyne Test

Solvent: 7 parts by weight of dimethylformamide
Emulsifier: 2 parts by weight of alkylaryl polyglycol ether To produce a suitable preparation of active compound, 1 part by weight of active compound is mixed with the stated amount of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematizidal activity is the determined in percent by the formation of galls. 100% means that no galls were found; 0% means that the number of galls on the treated plants corresponds to that of the untreated control.

In this test, for example, the following compounds of the Preparation Examples are highly effective: 3, 4, 5, 6, 7, 8, 9, 10, 11, 12, 13, 14, 15, 17, 18, 19, 20, 22, 23, 24, 25, 26, 27, 28, 29.

Compared to the prior art, the compounds according to the invention are, in the test described above, at a given concentration of active compound in ppm, clearly superior with respect to their efficacy (cf. Table II). The efficacy of the compounds is stated as kill rate in %.

| Compounds according to the invention | Compounds according to WO 00/03976 |
|---|---|
| [2,4-dichlorophenyl-CH(CH3)-N(CH3)-C(C2H5)=N-CN] Ex. 2 | [2,4-dichlorophenyl-CH(CH3)-N(H)-C(C2H5)=N-CN] |
| 20 ppm: 100% | 20 ppm: 0% |

-continued

| Compounds according to the invention | Compounds according to WO 00/03976 |
|---|---|
| Ex. 8 | |
| 4 ppm: 100% | 4 ppm: 0% |
| Ex. 17 | |
| 4 ppm: 100% | 5 ppm: 0% |

Example B

Spodoptera frugiperda Test

| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amount of solvent and emulsifier, and the concentrate is diluted with water to the desired concentration.

Cabbage leaves (*Brassica oleracea*) are treated by being dipped into the preparation of active compound of the desired concentration and are populated with caterpillars of the Heerwurms (*Spodoptera frugiperda*) while the leaves are still moist.

After the desired period of time, the kill in % is determined. 100% means that all caterpillars have been killed. 0% means that none of the caterpillars have been killed.

In this test, Preparation Examples 5, 9 and 19 are highly effective.

Example C

Phaedon Larvae Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed. 0% means that none of the beetle larvae have been killed.

In this test, for example, the following compounds of the Preparation Examples are highly effective: 19.

What is claimed is:

1. A compound of formula (I)

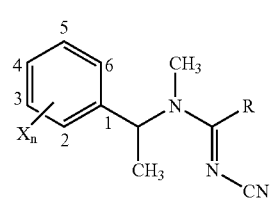

in which
n represents 2, 3, 4, or 5,
R represents optionally halogen-substituted $C_1$-$C_4$-alkyl, and
X represents halogen, where the different substituents X may be identical or different.

2. A process for preparing a compound of formula (I) as claimed in claim 1 comprising reacting a compound of formula (II)

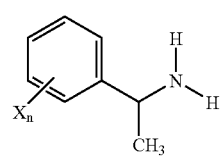

in which X and n are as defined for formula (I) in claim 1, with (a) a compound of formula (III)

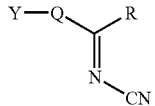

in which
R is as defined for formula (I) in claim 1,
Q represents oxygen or sulfur, and
Y represents alkyl, or (a') a compound of formula (IV)

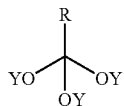

in which
R is as defined for formula (I) in claim 1, and
Y represents alkyl,
and cyanamide,
optionally in the presence of a diluent, and (b) alkylating the compound obtained according to steps (a) or (a') of the formula (V)

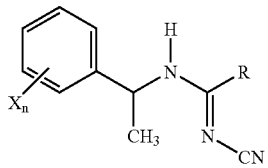

in which R, X, and n are as defined for formula (I) in claim 1, with a compound of formula (VI)

CH$_3$-Z    (VI)

in which Z represents a leaving group.

3. A process for preparing a compound of formula (I) as claimed in claim 1 comprising reacting a compound of formula (VII)

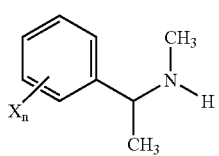

in which X and n are as defined for formula (I) in claim 1, with (a) a compound of formula (III)

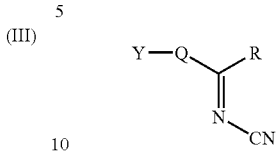

in which
R is as defined for formula (I) in claim 1,
Q represents oxygen or sulfur, and
Y represents alkyl, or (a') a compound of formula (IV)

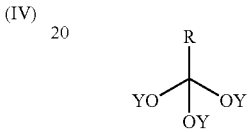

in which
R is as defined for formula (I) in claim 1, and
Y represents alkyl,
and cyanamide,
optionally in the presence of a diluent.

4. A compound of formula (I) as claimed in claim 1 in which
n represents 2, 3, or 4,
R represents optionally fluorine-, chlorine-, or bromine-substituted methyl, ethyl, n- or i-propyl, or n-, i-, s-, or t-butyl, and
X represents fluorine, chlorine, or bromine.

5. A compound of formula (I) as claimed in claim 1 in which
n represents 2 or 3,
R represents optionally fluorine- or chlorine-substituted methyl, ethyl, or n- or i-propyl, and
X represents fluorine or chlorine.

6. A compound of formula (I) as claimed in claim 1 in which R represents methyl or ethyl.

7. A pesticide comprising one or more compounds of formula (I) as claimed in claim 1 and one or more extenders and/or surfactants.

8. A method for controlling pests comprising allowing an effective amount of a compound of formula (I) as claimed in claim 1 to act on pests and/or their habitat.

9. A method for controlling pests comprising allowing an effective amount of a composition as claimed in claim 7 to act on pests and/or their habitat.

10. A process for preparing pesticides comprising mixing a compound of formula (I) as claimed in claim 1 with one or more extenders and/or surfactants.

* * * * *